US012807643B2

(12) United States Patent
Atlas

(10) Patent No.: US 12,807,643 B2
(45) Date of Patent: Nov. 24, 2026

(54) DOPAMINE PRECURSORS

(71) Applicant: Yissum Research Development Company of the Hebrew University of Jerusalem Ltd., Jerusalem (IL)

(72) Inventor: Daphne Atlas, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 18/172,333

(22) Filed: Feb. 22, 2023

(65) Prior Publication Data

US 2023/0192764 A1 Jun. 22, 2023

Related U.S. Application Data

(63) Continuation of application No. 16/968,022, filed as application No. PCT/IL2019/050146 on Feb. 6, 2019, now abandoned.

(60) Provisional application No. 62/627,879, filed on Feb. 8, 2018, provisional application No. 62/627,886, filed on Feb. 8, 2018.

(51) Int. Cl.

| | |
|---|---|
| ***C07K 5/083*** | (2006.01) |
| ***A61P 25/16*** | (2006.01) |
| ***A61P 25/28*** | (2006.01) |
| ***C07K 5/062*** | (2006.01) |
| *A61K 38/00* | (2006.01) |

(52) U.S. Cl.

CPC .............. *C07K 5/081* (2013.01); *A61P 25/16* (2018.01); *A61P 25/28* (2018.01); *C07K 5/0606* (2013.01); *A61K 38/00* (2013.01)

(58) Field of Classification Search

CPC ....... C07K 5/081; C07K 5/0606; A61P 25/16; A61P 25/28; A61K 38/00

See application file for complete search history.

(56) References Cited

FOREIGN PATENT DOCUMENTS

WO WO-2013063615 A2 * 5/2013 ............. A61K 31/07

OTHER PUBLICATIONS

Alba Minelli, N-Acetyl-L-Methionyl-L-Dopa-Methyl Ester as a dual acting drug that relieves L-Dopa-induced oxidative toxicity, Free Radical Biology & Medicine 49 (2010) 31-39.*

Janusz Lipski, L-DOPA: A scapegoat for accelerated neurodegeneration in Parkinson's disease?, Progress in Neurobiology 94 (2011) 389-407.*

Genscript, Peptide Modification services, 2010.*

Serge Przedborski, Neurodegeneration: What is it and where are we?, J. Clin. Invest. 111:3-10 (2003).*

Francesco Pinnen, Codrugs Linking L-Dopa and Sulfur-Containing Antioxidants: New Pharmacological Tools against Parkinson's Disease, J. Med. Chem. 2009, 52, 559-563.*

Sang-Eun Park et al., "Control of mammalian G protein signaling by N-terminal acetylation and the N-end rule pathway", Science 347(6227), Publication Date: Mar. 13, 2015 (Mar. 13, 2015), pp. 1249-1252.

Daniel Offen et al., "A low molecular weight copper chelator crosses the blood-brain barrier and attenuates experimental autoimmune encephalomyelitis", Journal of Neurochemistry, 2004, 89, 1241-1251 doi:10.1111/j.1471-4159.2004.02428.x.

Parkinson Study Group, "A Randomized Controlled Trial of Etilevodopa in Patients With Parkinson Disease Who Have Motor Fluctuations", (Reprinted) Arch Neurol/vol. 63, Feb. 2006, pp. 210-216.

Tom Wiesen and Daphne Atlas, "Novel anti-apoptotic L-DOPA precursors SuperDopa and SuperDopamide as potential neuroprotective agents for halting/delaying progression of Parkinson's disease", Cell Death and Disease (2022) 13: 227, pp. 1-12.

* cited by examiner

*Primary Examiner* — Erinne R Dabkowski

(74) *Attorney, Agent, or Firm* — JMB Davis Ben-David

(57) ABSTRACT

The invention disclosed herein concerns a novel class of compounds suitable for the treatment of neurodegenerative diseases, such as Parkinson's Disease.

1 Claim, 8 Drawing Sheets

DOPAMINE PRECURSORS

CROSS REFERENCE TO RELATED APPLICATIONS

This is a Continuation of U.S. patent application Ser. No. 16/968,022, filed Aug. 6, 2020, which is the US National Stage of International Patent Application No. PCT/IL2019/050146, filed Feb. 6, 2019, and which in turn claims priority to U.S. Provisional Patent Application No. 62/627,886, filed Feb. 8, 2018, and U.S. Provisional Patent Application No. 62/627,879, filed Feb. 8, 2018. The contents of the foregoing patent applications are incorporated by reference herein in their entirety.

TECHNOLOGICAL FIELD

The invention generally concerns compounds useful in the treatment of neurodegenerative diseases or disorders.

BACKGROUND

Parkinson's Disease (PD) is characterized by the preferential vulnerability and loss of dopaminergic nigrostriatal projection neurons. Several cellular mechanisms were suggested to the initiation of PD. These include oxidative stress and mitochondrial stress. Levodopa, also called L-dopa, which is converted to dopamine in the brain, remains the gold standard for treating Parkinson's disease. However, this current treatment of PD, which uses mainly a combination of levodopa/carbidopa, aiming at replenishing the missing dopamine, is an efficient symptomatic treatment, which does not prevent the progression of the disease.

In addition, a large number of the side effects result from the insolubility of L-dopa and the frequent use of large doses. For example, L-dopa is poorly absorbed and may remain in the stomach for long periods of time. Some studies suggest induction of oxidative cell death during L-dopa/dopamine degradation, presenting an additional difficulty with L-dopa treatment. Toxicity of L-dopa also contributes to the premature death of the dompaminergic cells in the substantia nigra.

L-dopa is poorly absorbed and once it gets into the brain it is immediately converted to dopamine and, in part, could lead to on/off fluctuations. In addition, within 4 to 6 years of treatment with L-dopa, the effects in many patients begin to fade out with the effect of the next dose wearing off more quickly; this is referred to as the wearing-off effect. In addition, the dopaminergic neurons continue to deteriorate and eventually disappear by premature death. The loss of the dopaminergic cells is partly attributed to ROS production by hydrolysis of dopamine. The oxidized environment at the dopaminergic cells leads to apoptosis and further deteriorations of the cells.

A number of strategies have been developed to overcome some of these observed difficulties. For some patients, use of a liquid form of a combination of L-dopa and carbidopa (Sinemet) produces fewer fluctuations and a prolonged "on" time as compared with a tablet dose. However, there is no treatment for protecting the cells from premature death.

One of the major and most critical unmet needs in the treatment protocols of PD is to arrest the progression of the disease by saving dopaminergic neurons from cell death and to prevent or at least lower fluctuations of L-dopa levels in the blood and in the brain for maintaining a consistent level of dopamine.

BACKGROUND ART

[1] U.S. Pat. No. 3,803,120

[2] International patent application no. WO2006/056604

[3] International patent application no. WO2009/007696

[4] U.S. Pat. No. 5,073,547

[5] U.S. Pat. No. 4,065,566

[6] International patent application no. WO2007/091017

[7] International patent application no. WO2013/168021

[8] International patent application no. WO2013/017974

[9]U.S. Pat. No. 8,304,452.

GENERAL DESCRIPTION

It is thus the purpose of the invention disclosed herein to introduce a novel class of compounds that is stable and effective in preventing cell death by inhibiting the apoptotic pathway, and that acts as means for delivery of L-dopa in a slow release mode. The water-solubility and the amide form of the L-dopa derivatives of the invention have demonstrated several advantages, including stability and bioavailability, over standard L-dopa treatment of neurodegenerative diseases, such as PD.

Treatment modalities using compounds of the invention provide means for saving neuronal cells, e.g., dopaminergic neurons, from cell death, concomitantly with providing the dopaminergic cells with L-dopa. These are achievable by providing a steady supply of L-dopa to the brain and thus preventing the wearing-off effects of L-dopa while protecting dopaminergic neurons from cell death in the substantia nigra.

Thus, in a first aspect there is provided a compound of the general formula (I):

(I)

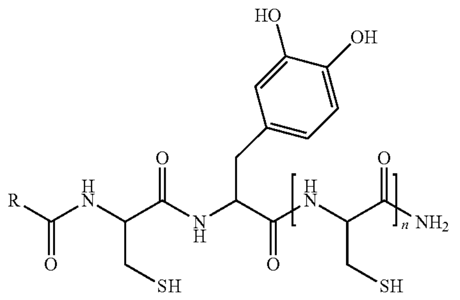

wherein

R is a $C_1$-$C_5$alkyl; and n is zero or 1.

A compound wherein R is methyl and n is 0 is excluded from novel compounds of the invention.

In some embodiments, n is 1.

In some embodiments, the $C_1$-$C_5$alkyl is selected from methyl, ethyl, propyl, butyl and pentyl. In some embodiments, the $C_1$-$C_5$alkyl is selected from methyl, n-butyl, iso-propyl, tert-butyl and n-pentyl. In some embodiments, the $C_1$-$C_5$alkyl is methyl.

In some embodiments, n is 1 and R is methyl.

It is understood that compounds provided herein contain chiral centers. Such chiral centers may be of either the (R) or (S) configuration, or may be a mixture thereof. Thus, compounds provided herein may be provided in enantiomerically pure form, or in stereoisomeric or diastereomeric mixtures. It should also be understood that the compounds may undergo epimerization in vivo. Therefore, administration of a compound in, e.g., its (R) form is equivalent, for compounds that undergo epimerization in vivo, to administration of the compound in its (S) form, and vice versa.

Additionally, each of the amino acid residues may be of either the L- or D-form.

Compounds of the invention may be provided in a 'free base' or 'free acid' form, namely in a protonated/alkylated or non-protonated/non-alkylated form or may be presented in the form of a pharmaceutically acceptable salt. Such salts may be derived from inorganic acids such as hydrochloric, nitric, phosphoric, sulfuric, hydrobromic, hydriodic, phosphorous, and the like, as well as salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. These salts may include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and others. For additional salts see Berge S. M., et al., "Pharmaceutical Salts," J. of Pharmaceutical Science, 66:1-19 (1977).

Compounds of the invention may be regarded as L-dopa depot or pro-drugs of L-dopa, serving as precursors of dopamine. The hydrolysis of the amide bond(s) is a rate limiting reaction that is responsible for a slow production of L-dopa and dopamine, ensuring a steady level of dopamine delivery to the brain.

Compounds of the invention further present a redox activity that may be attributed to the presence of one or two cysteine residues (Cys). Each of the one or two residues is a reactive oxygen species (ROS) scavenger and an inhibitor of ROS production by virtue of its chelating ability of copper and zinc. This anti-apoptotic property protects the dopaminergic neurons from premature death. The presence of the one or two Cys residues, with the adjacent peptide bonds also renders the compounds capable of denitrosylating proteins such as MEF-2C. As known in the art, MEF-2C is a transcription factor that is nitrosylated by alpha-synuclein and mitochondrial-targeted toxins and plays a major role in initiating neuronal cell death that is associated with Parkinson's disease.

The compounds are effective inhibitors of the auranofin-induced inflammatory mitogen activated protein kinases (MAPK) pathway in particular the JNK and $P38^{MAPK}$ triggering apoptosis.

It is therefore the purpose of the invention to provide a composition, preferably a pharmaceutical composition, that comprises a compound of general formula (I).

Compositions of the invention may further comprise suitable additives such as vehicles, adjuvants, excipients, or diluents, as well-known to those skilled in the art. The pharmaceutically acceptable carrier is one which is chemically inert to the active compounds and one which has no detrimental side effects or toxicity under the conditions of use.

The choice of carrier will be determined in part by the particular compound of the invention used in the composition, as well as by the particular method used to administer the composition. Accordingly, there is a wide variety of suitable formulations of the pharmaceutical composition of the present invention. Compositions for oral, aerosol, inhalation, nasal, parenteral, subcutaneous, transdermal administration (e.g. patch), intradermal, intravenous, intramuscular, buccal, intraperitoneal, rectal and vaginal administration are merely exemplary and are in no way limiting.

In some embodiments, compounds and compositions of the invention are suitable or adapted for oral administration.

Compositions for oral administration may comprise of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia, as well as pastilles comprising the active ingredient in an inert base, such as gelatin and glycerin, or sucrose and acacia, emulsions, gels, and the like containing, in addition to the active ingredient, such carriers as are known in the art.

Compounds of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer Compositions suitable for parenteral administration include aqueous and non-aqueous, isotonic sterile injection solutions, which can contain anti-oxidants, buffers, bacteriostats and solutes that render the formulation isotonic with the blood of the intended recipient, and aqueous and non-aqueous sterile suspensions that include suspending agents, solubilizers, thickening agents, stabilizers, and preservatives. The compounds can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils for use in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

Parenteral formulations may contain preservatives and buffers and one or more nonionic surfactants having a hydrophile-lipophile balance (HLB) of from about 12 to about 17 that reduce irritation upon administration. The quantity of surfactant in such formulations may vary. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Compounds of the present invention may be made into injectable formulations, the requirements for which are known in the art. See for example *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, $4^{th}$ ed., pages 622-630 (1986).

As demonstrated herein, compounds of the invention have been found to be effective in protecting cells from the auranofin-induced morphological changes, most likely caused by oxidative stress. In the model used, auranofin inhibits thioredoxin reductase and induces oxidative stress by preventing thioredoxin from regaining its reduced and active state. One of the major contributors to neurodegenerative diseases such as Parkinson's disease (PD) is an increase in the oxidative and inflammatory states of the cell. This model was used to study the potency and potential of the compounds to reverse oxidative/inflammatory induced cell death.

Thus, compounds of the invention or compositions comprising them may be used in a method of protecting cells from auranofin-induced morphological changes. The invention further concerns use of a compound or composition of the invention in a method of reducing or reversing oxidative stress or an inflammatory state of a human or animal cell, in vivo.

By either protecting cells from these morphological changes, or by decreasing or reversing oxidative state or inflammatory states of the human or animal cells, compounds of the invention are, indirectly or directly, capable of treating a neurodegenerative disease or disorder, or a disease or disorder characterized by or associated with reduced levels of brain dopamine.

As used herein, a "neurodegenerative disease or disorder, or a disease or disorder characterized by or associated with reduced levels of brain dopamine" refers to a disease or disorder that is caused by damage to the central nervous system and can be identified by progressive dysfunction, degeneration and death of specific populations of neurons which are often synaptically interconnected. Non-limiting examples of such neurodegenerative diseases and disorders include Huntington's disease, spinocerebellar ataxias, Parkinson's disease, secondary parkinsonism, morbus Alzheimer, progressive supranuclear palsy (PSP), multiple system atrophy (MSA), amyotrophic lateral sclerosis (ALS), Shy Drager syndrome, dopamine-responsive dystonia, cystic fibrosis, familial amyloidotic polyneuropathy, spongiform encephalopathies, dementia with Lewy body disease (LBD), akinesia, bradykinesia, hypokinesia, frontotemporal dementia with Parkinsonism, spinocerebellar ataxias, spinal and bulbar muscular atrophy, hereditary dentatorubral-pallidoluysian atrophy, familial British dementia, familial Danish dementia, prion disease, mild brain trauma mTBI, atherosclerosis and allergic airway disease.

In some embodiments, compounds of the invention are used in the treatment of Parkinson's disease and dopamine-responsive dystonia.

In another aspect there is provided a method of treating a neurodegenerative disease or disorder or a disease or disorder characterized by or associated with reduced levels of brain dopamine, as described herein, the method comprising administering an effective amount of a compound of the general formula (I) to a subject suffering from such a disease or disorder or a subject having disposition to suffering from such a disease or disorder or to a subject demonstrating one or more symptoms associated with early manifestation of such a disease or disorder.

In some embodiments, a compound of the general formula (I) is a compound wherein R is a $C_1$-$C_5$alkyl and n is zero or 1. In some embodiments, n is 1 and in some other embodiments, n is zero. In some embodiments, the $C_1$-$C_5$alkyl is selected from methyl, ethyl, propyl, butyl and pentyl. In some embodiments, the $C_1$-$C_5$alkyl is selected from methyl, n-butyl, iso-propyl, tert-butyl and n-pentyl. In some embodiments, the $C_1$-$C_5$alkyl is methyl. In some embodiments, n is zero or 1 and R is methyl.

In some embodiments, the compound of general formula (I) is a compound herein designated (II) and in some other embodiments, the compound is a compound herein designated (III):

(II)

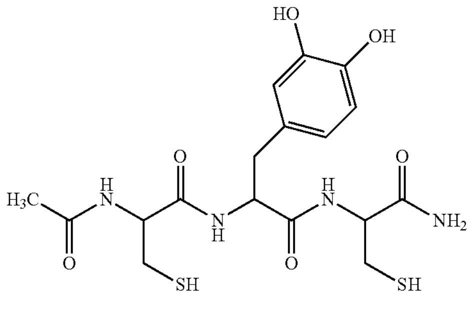

-continued (III)

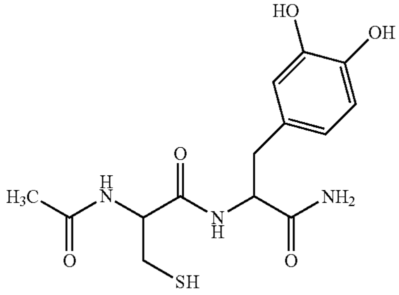

The term "treatment" as used herein refers to the administering of a therapeutic amount of a composition of the present invention or of a compound of the invention which is effective to ameliorate undesired symptoms associated with a disease, as disclosed, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above, and lower the frequency of medication currently used with levodopa.

The "effective amount" for purposes herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half-life in the body, on undesired side effects, if any, on factors such as age and gender, etc.

Thus, according to some embodiments of the invention, there is provided a compound of the general formula (I):

(I)

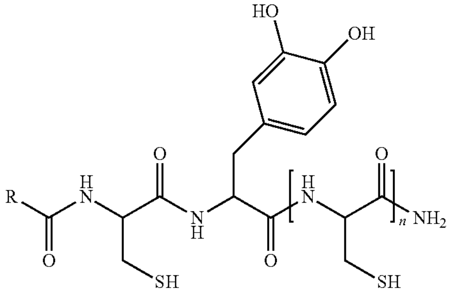

wherein

R is a $C_1$-$C_5$alkyl; and n is zero or 1, excluding a compound wherein n is 0 and R is methyl.

In some embodiments, n is 1.

In some embodiments, $C_1$-$C_5$alkyl is selected from methyl, ethyl, propyl, butyl and pentyl. In some embodiments, $C_1$-$C_5$alkyl is selected from methyl, n-butyl, iso-propyl, tert-butyl and n-pentyl. In some embodiments, $C_1$-$C_5$alkyl is methyl.

In some embodiments, n is 1 and R is methyl.

Also provided is a L-dopa precursor of dopamine having a structure according to formula (I).

An inhibitor of oxidative induced inflammatory mitogen activated protein kinases (MAPK) pathway is also provided that has a structure according to formula (I). In some embodiments, the MAPK is JNK and $P38^{MAPK}$.

Also provided is a composition comprising a compound of formula (I). In some embodiments, the composition is a pharmaceutical composition, optionally adapted for oral administration, administration by an aerosol, administration by inhalation, nasal administration, parenteral administration, subcutaneous administration, transdermal administration, intradermal administration, intravenous administration, intramuscular administration, buccal administration, intraperitoneal administration, rectal administration or vaginal administration. In some embodiments, the formulation/composition is suitable for oral administration.

In some embodiments, the composition is for use in protecting cells from oxidative stress.

Compounds of formula (I) may be used in vivo methods of reducing or reversing oxidative stress, or an inflammatory state of a human or animal cell, e.g., for treating a neuro-degenerative disease or disorder, or a disease or disorder characterized by or associated with reduced levels of brain dopamine.

Thus, a method is provided for reducing or reversing oxidative stress, or an inflammatory state of a human or animal cell, the method comprising treating a subject with a compound of the formula (I):

(I)

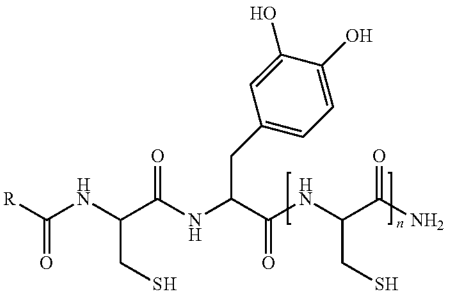

wherein

R is a $C_1$-$C_5$alkyl; and n is zero or 1.

In some embodiments, the method is for treating a disease or disorder characterized by or associated with reduced levels of brain dopamine.

A method for treating a neurodegenerative disease or disorder, or a disease or disorder characterized by or associated with reduced levels of brain dopamine, comprises administering a compound to a subject suffering therefrom or having disposition to suffering therefrom, wherein the compound is of the general formula (I):

(I)

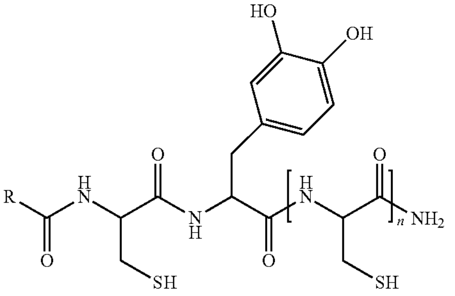

wherein

R is a $C_1$-$C_5$alkyl; and n is zero or 1.

In some embodiments, the disease or disorder is caused by damage to the central nervous system. In some embodiments, the disease or disorder is characterized by progressive dysfunction, degeneration and death of neurons optionally synaptically interconnected. In some embodiments, the disease or disorder is associated or based on oxidative stress, or an inflammatory state of a human or animal cell. In some embodiments, the disease or disorder is associated with reduced levels of brain dopamine.

In some embodiments, the neurodegenerative diseases and disorders is selected from Huntington's disease, spinocerebellar ataxias, Parkinson's disease, secondary parkinsonism, morbus Alzheimer, progressive supranuclear palsy (PSP), multiple system atrophy (MSA), amyotrophic lateral sclerosis (ALS), Shy Drager syndrome, dopamine-responsive dystonia, cystic fibrosis, familial amyloidotic polyneuropathy, spongiform encephalopathies, dementia with Lewy body disease (LBD), akinesia, bradykinesia, hypokinesia, frontotemporal dementia with Parkinsonism, spinocerebellar ataxias, spinal and bulbar muscular atrophy, hereditary dentatorubral-pallidoluysian atrophy, familial British dementia, familial Danish dementia, prion disease, mild brain trauma mTBI, atherosclerosis, and allergic airway disease.

In some embodiments, the disease or disorder is Parkinson's disease or dopamine-responsive dystonia.

In some embodiments, the compound used in methods of the invention is a compound wherein R is a $C_1$-$C_5$alkyl and n is zero or 1. In some embodiments, n is 1. In some embodiments, n is zero. In some embodiments, $C_1$-$C_5$alkyl is selected from methyl, ethyl, propyl, butyl and pentyl. In some embodiments, $C_1$-$C_5$alkyl is selected from methyl, n-butyl, iso-propyl, tert-butyl and n-pentyl. In some embodiments, $C_1$-$C_5$alkyl is methyl. In some embodiments, n is zero or 1 and R is methyl. In some embodiments, the compound is:

(II)

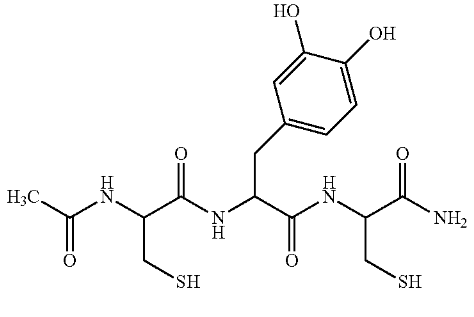

or

-continued (III)

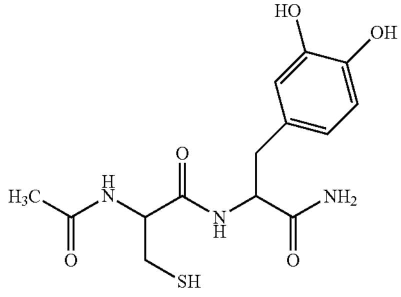

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

(FIG. 7A) Control untreated PC12 cells (FIG. 7B). PC12 cells were treated with AuF (2 μM; 30 min) lose their morphology and become rounded, as compared to untreated cells. (FIG. 7C) AuF-treated (2 μM; 30 min) cells incubated with 150 μM SDA showed normal morphology (magnification ×100 and ×200). Cells were treated with AuF (2 μM) for 30 min, washed and then SDA was added at 25 μM or 100 μM. Cells were visualized 4 hr later (magnification, 100× and 400×).

DETAILED DESCRIPTION OF EMBODIMENTS

Results

Synthesis

Figure 1:
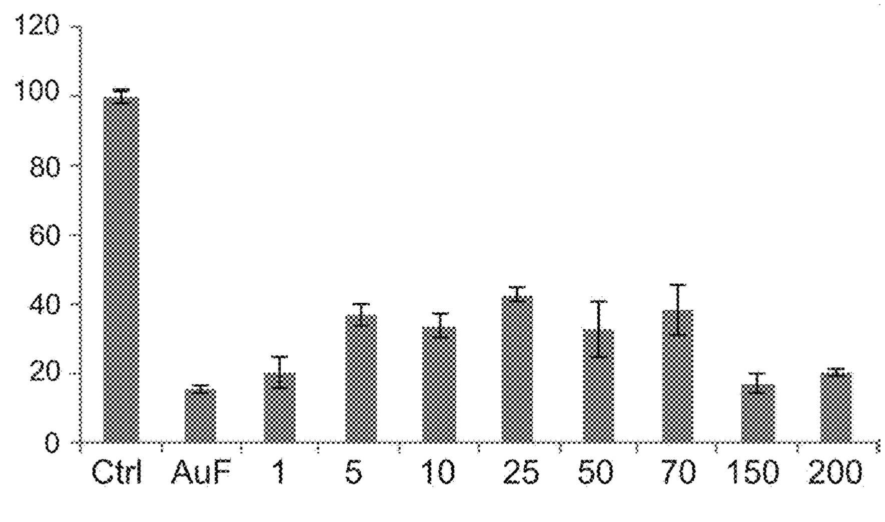
FIG. 1 demonstrates the ability of compound SD-444 to rescue human neuroblastoma cells (SH-SY5Y) from auranofin- (AuF) induced cell death. Viability of cells pre-treated with 5 μM AuF for 30 min, washed and later exposed to increasing concentrations of SD-444, was determined 24 h later. Data is displayed as mean±S.E.M.

Acetyle-Cys-2,3 dihydroxyphenylalanin-Cys-amide (SD-444) was prepared by standard peptide synthesis procedure.

SD-444 was tested for protecting neuronal cells from activating apoptotic signaling:

A) The anti-apoptotic activity of SD-444 was tested on human neuronal cells SH-SY5Y. The cells were challenged by auranofin (AuF) that induces cellular stress by selectively blocking the thioredoxin reductase activity.

SH-SY5Y cells were plated on 96-well plates and treated with AuF in different concentrations for 30 min. Then the cells were washed with PBS and treated as indicated. Twenty-four hours later, the cells were fixed with glutaraldehyde in final concentration of 0.5% for 10 min. Cells were washed 3 times with DDW dried overnight, and washed once with borate buffer (0.1 M, pH 8.5). The fixed cells were stained with 200 μl of 1% methylene blue dissolved in borate buffer for 1 h. After extensive washing and drying, the color was extracted with 200 μl of 0.1 M HCl for 1 h at 37° C. and absorbance was read in spectrophotometer at 630 nm.

When SD-444 was applied to the cells, the AuF effect was partially reversed and neuronal cell-viability was partially restored (FIG. 1).

B) The ability of SD-444 to prevent apoptosis was monitored and the molecular mechanism through which it exerts protection of the cells was identified to be the ASK-MAPK pathway.

In the assay, twenty to thirty micrograms of protein samples were loaded on 10-12% SDS-PAGE gels. The proteins were then transferred electrophoretically to nitrocellulose (Whatman, Germany). The blots were blocked by incubation for 1 h at RT in TBS-T (25 mM Tris-HCl pH 7.4, 0.9% NaCl and 0.02% Tween-20) with 4% Difco skim milk (BD, USA), and incubated over-night at 4° C. with the primary antibody: p-p38$^{MAPK}$ (Thr180/Tyr182), rabbit mAb; p38, rabbit Ab.

Figure 2:
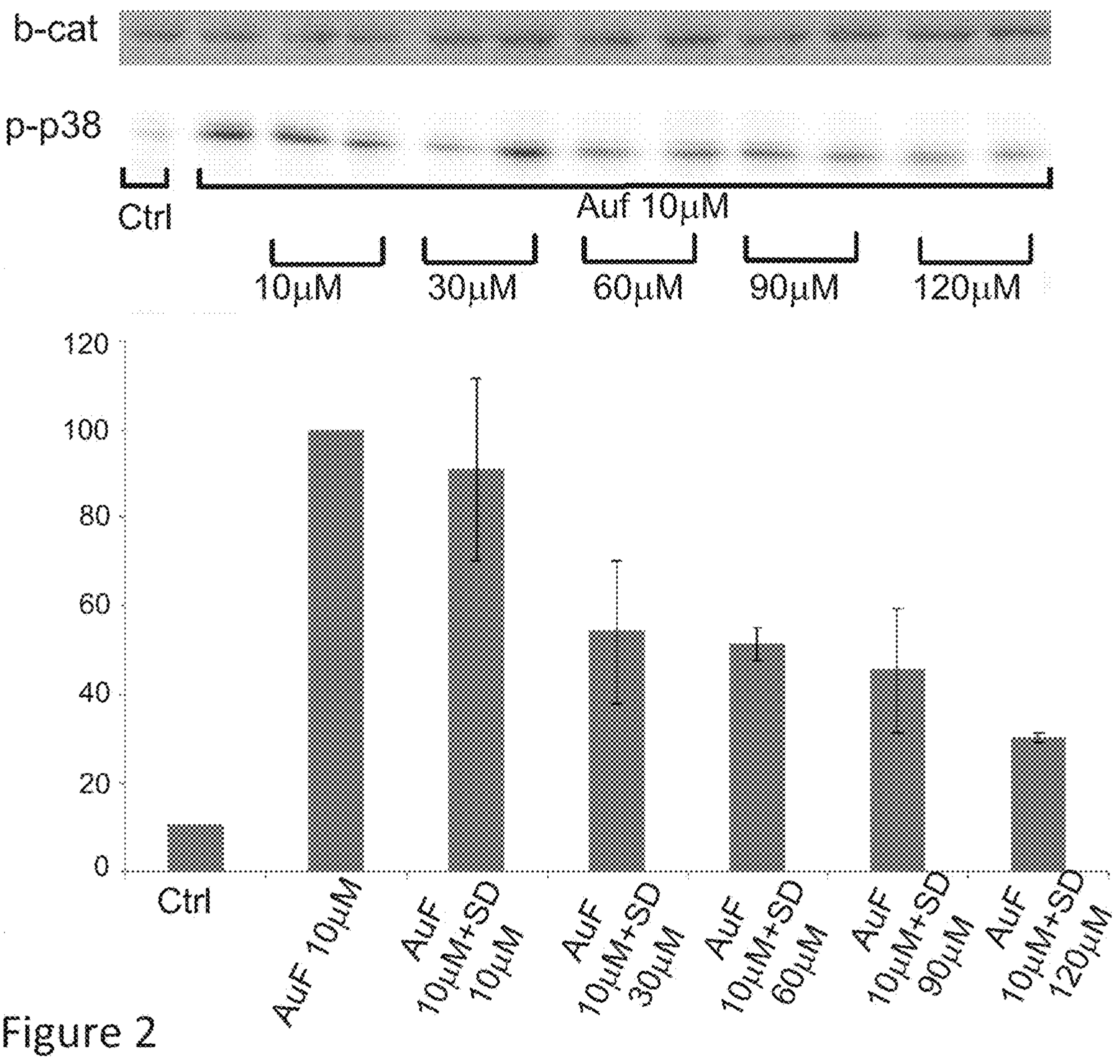
FIG. 2 demonstrates the ability of SD-444 to protect human neuroblastoma cells (SH-SY5Y) from oxidative stress induced inflammation, as shown by inhibition-induced phosphorylation of $p38^{MAPK}$. Cells were treated with 10 M AuF with or without SD-444. Phosphorylation was determined by western blot analysis. The amount of each band was quantitated by densitometry and plotted with a linear regression program normalized with β catenin (b-cat).
Figure 3:
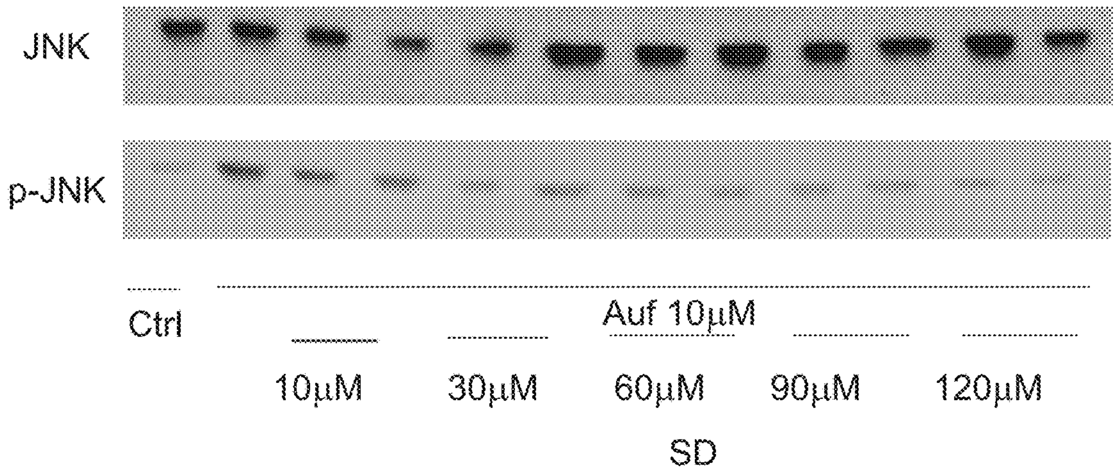
FIG. 3 demonstrates the ability of SD-444 to protect cells from oxidative stress by inhibition-induced phosphorylation of JNK. SH-SY5Y cells were treated with 10 M AuF with or without SD-444. Phosphorylation was determined by western blot analysis. The amount of each band was quantitated by densitometry and plotted with a linear regression program normalized to total JNK.
Figure 3:
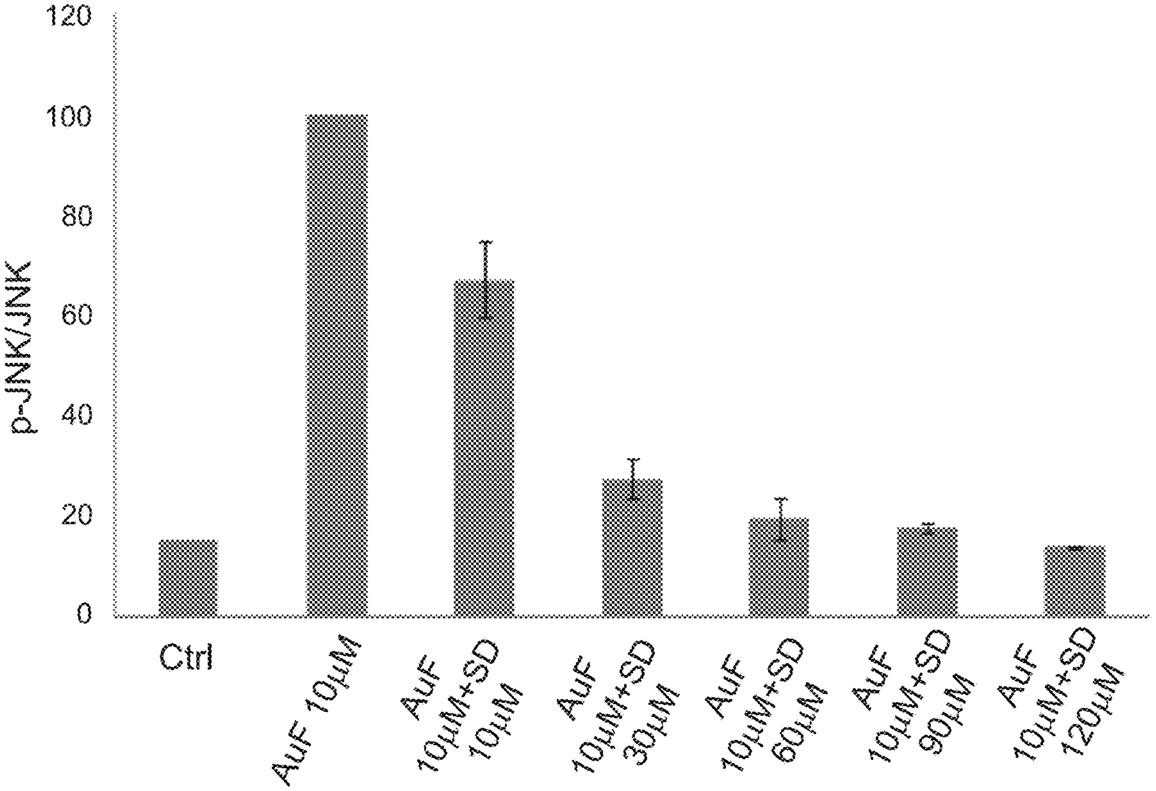

As shown in FIG. 2 and FIG. 3, stress induced by AuF in the neuronal SH-SY5Ycells led to the activation of cell-death pathways through the activation of MAPK p38 and JNK. In cells treated with SDA-444 there was a significant reduction in p38 activation already at 30 μM (FIG. 2) and at 10 μM in JNK (FIG. 3).

C) Phase microscopy studies: The ability of SD-444 to rescue cells from oxidative stress was tested by exposing the PC12 to 2 μM auranofin for 30 min, and after washing incubated with 250 μM SD-444 at 37° C. for additional 4 hrs.

Figure 4:
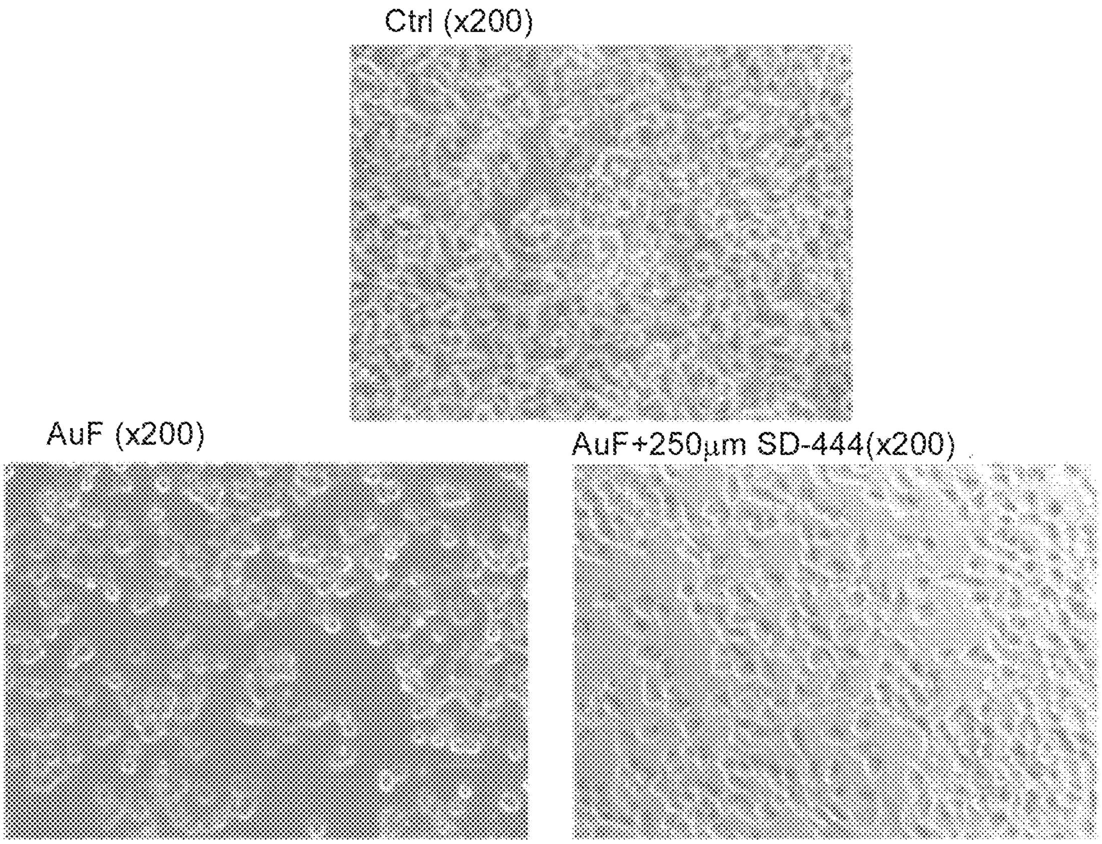
FIG. 4 demonstrates the reversal of morphological changes in PC12 cells by oxidative stress, by utilizing SD-444. PC12 cells were treated with AuF with or without SD-444. Morphological changes were visualized 4 hr later (magnification ×200).

As shown in FIG. 4, cells that were incubated with AuF and then with SD-444 showed similar morphology to untreated cells, as opposed to cells that were exposed to auranofin, which looked rounded, losing normal morphology.

Acetyle-Cys-2,3 dihydroxyphenylalanine-amide (SDA-341) was synthesized, purified, and chemically analyzed. SDA-341 was prepared by the conventional standard liquid-phase method.

Activity of SDA-341

SDA-341 was tested for protecting neuronal cells from activating apoptotic signaling:

A) The ability of SDA-341 to prevent apoptosis was monitored and the molecular mechanism through which it exerts protection of the cells was identified to be the ASK-MAPK pathway.

In the assay, twenty to thirty micrograms of protein samples were loaded on 10-12% SDS-PAGE gels. The proteins were then transferred electrophoretically to nitrocellulose (Whatman, Germany). The blots were blocked by incubation for 1 h at RT in TBS-T (25 mM Tris-HCl pH 7.4, 0.9% NaCl and 0.02% Tween-20) with 4% Difco skim milk (BD, USA), and incubated over-night at 4° C. with the primary antibody: p-JNK$^{MAPK}$, and β-catenin.

Figure 5:
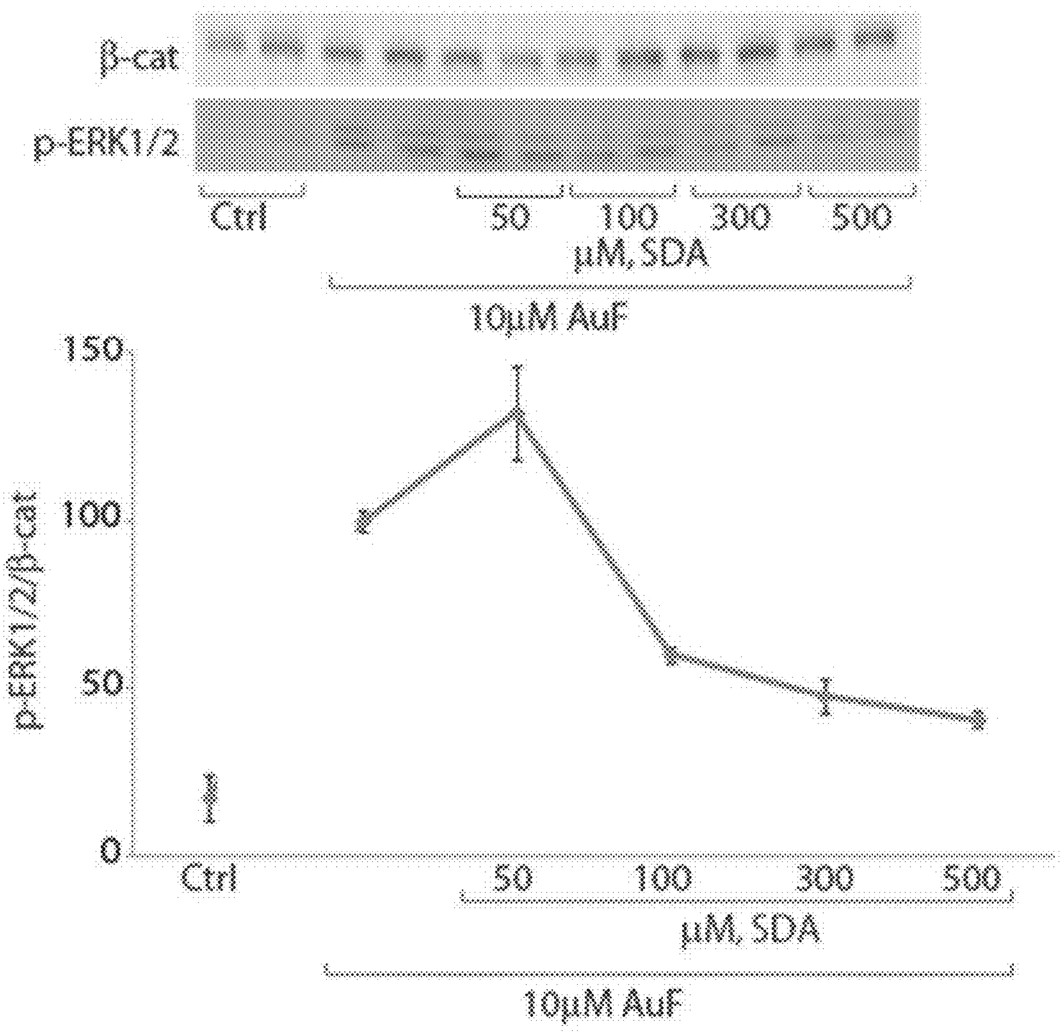
FIG. 5 demonstrates the ability of SDA-341 to protect human neuroblastoma cells (SH-SY5Y) from oxidative stress induced inflammation, as shown by inhibition-induced phosphorylation of ERK1/2. SH-SY5Y cells were treated with 10 μM AuF with or without SDA-341. Phosphorylation was determined by western blot analysis. The amount of each band was quantitated by densitometry and plotted with a linear regression program normalized to beta-catenin.

As shown in FIG. 5 stress induced by AuF in the neuronal SH-SY5Y cells leads to the activation of cell-death pathways through the activation of MAPK JNK. In cells treated with SDA-341 $EC_{50}$ of 100 μM in reduction of JNK activation.

Figures 6A, 6B, 6C:
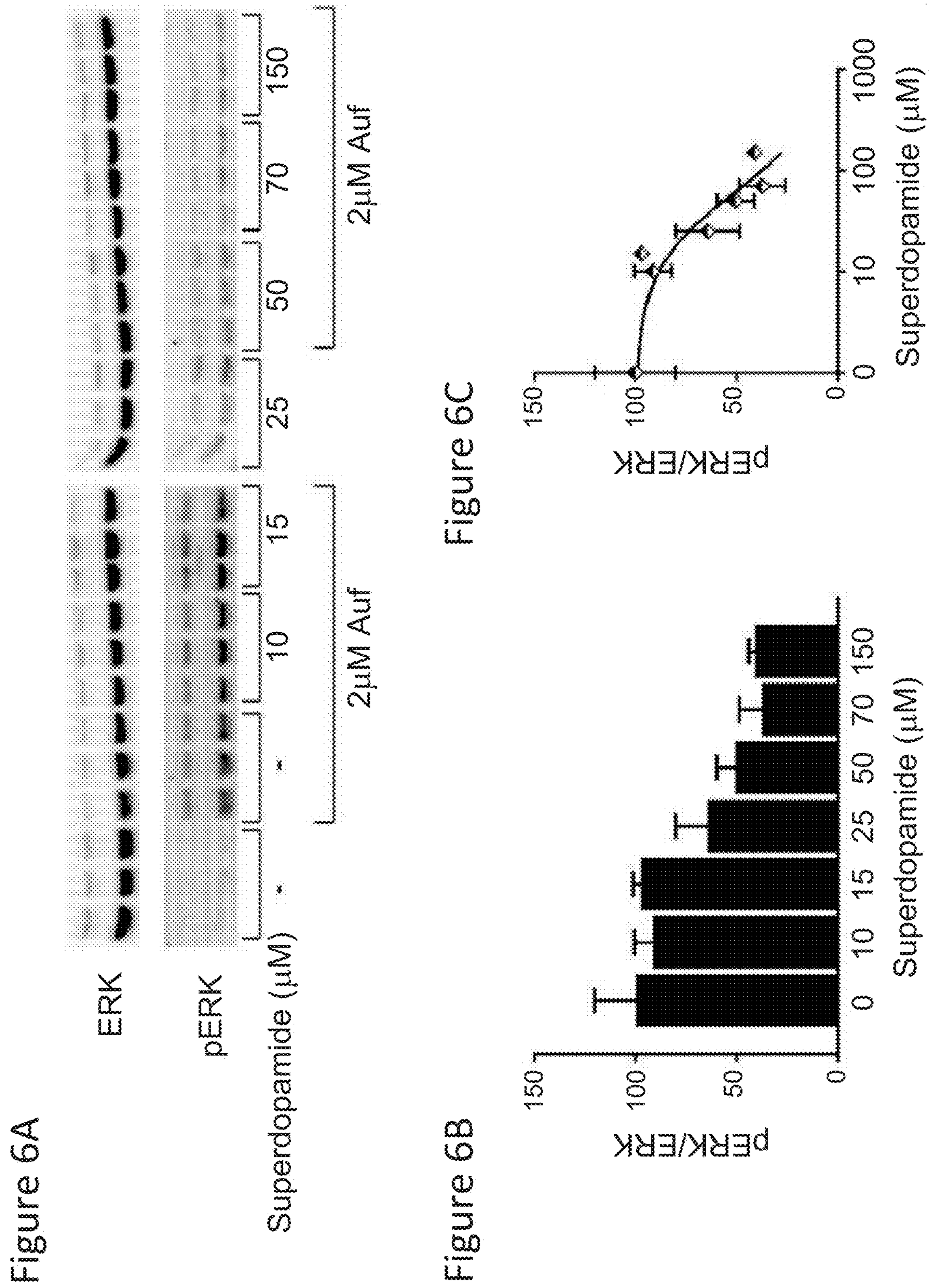
FIGS. 6A-C demonstrate the ability of SDA-341 to protect PC12 cells from oxidative stress induced inflammation, as shown by inhibiting auranofin-induced phosphorylation of ERK1/2. Cells were treated with 10 M AuF with or without SDA-341. Phosphorylation was determined by western blot analysis (FIG. 6A). The amount of each band was quantitated by densitometry (FIG. 6B) and plotted with a linear regression program normalized to total ERK2 (FIG. 6C).

The ability of SDA-341 to lower AuF induced activation of ERK1/2 in PC12 cells with the corresponding anti ERK1/2 and ERK2 antibodies was also tested, as shown in FIG. 6. Calculated $EC_{50}$=80 μM.

B) Phase microscopy studies: The ability of SDA to rescue the cells from oxidative stress was tested by exposing the PC12 to auranofin 2 μM for 30 min with or without 150 μM SDA. AuF was washed after 30 min and 150 μM SDA was added and allowed to incubate at 37° C. for additional 4 hrs.

Figure 7A:
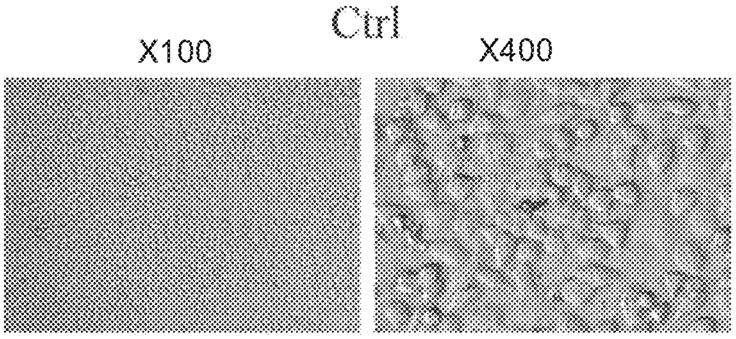
FIGS. 7A-C demonstrate the reversal of morphological changes in PC12 cells by oxidative stress, by utilizing SDA.
Figure 7B:
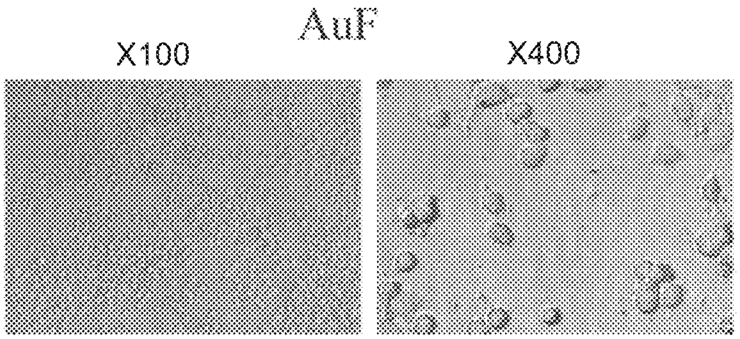
Figure 7C:
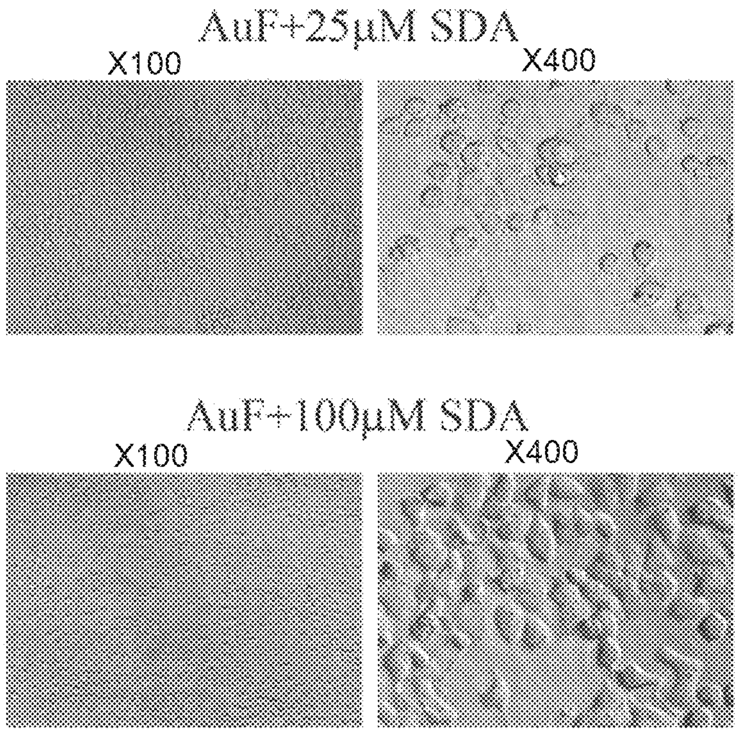

Phase microscopy showed the morphology of the cells after 4 hrs as shown in FIG. 7. PC12 cells incubated with SDA displayed a similar morphology to un-treated cells, as opposed to cells that were exposed to AuF, which looked rounded loosing normal morphology.

Animal Study: Purpose

The aim of this study was to examine the efficacy of two new compounds, SuperDopa (SD; 444) and Superdopamide (SDA; 341) in protecting neuronal pathways in vivo, using a Rotenone-induced model of Parkinson's disease (PD) in rats. The study was performed with Sprague Dawley rats (Tables 1 and 2).

TABLE 1

| Test System | |
|---|---|
| Species/Strain: | Sprague Dawley rats |
| Source: | Envigo |
| Sex: | Males |
| Total No. of Animals: | 20 |
| Age: | 7-9 weeks of age at treatment administration. |
| Body Weight: | 292-315 g at study initiation. Weight variation of animals at the time of treatment initiation should not exceed ± 20% of the required weight. |
| Acclimation period: | 7 days. |
| Animals Health: | Only animals in good health acclimatized to laboratory conditions for 7 days were used in the study. Animals with any evidence of disease or physical abnormalities were not selected for study. |

TABLE 2

| Utilities and environmental control | |
|---|---|
| Animal Housing: | Housing: Animal handling was performed according to guidelines of the National Institute of Health (NIH) and the Association for Assessment and Accreditation of Laboratory Animal Care (AAALAC). Animals are housed in cages polysulphone (3/cage) measuring 425 × 266 × 185 mm, with stainless steel top grill facilitating pelleted food and drinking water in plastic bottle; bedding: steam sterilized clean paddy husk (Harlan, Sani-chip, Cat#: 7090A) was be used and bedding material was changed along with the cage at least twice a week. |
| Environment: | Automatically controlled environmental conditions were set to maintain temperature at 22 −/+2 °C with a relative humidity (RH) of 55 −/+15%, a 12:12 hour light:dark cycle and 10-30 air changes/hr in the study room. |
| Identification: | Animals were given a unique animal identification number. This number also appeared on a cage card, visible on the front of each cage. The cage card also contained the study number, route of administration and all other relevant details as to treatment group and dose level. |

TABLE 2-continued

| Utilities and environmental control | |
|---|---|
| Diet and water: | Animals are provided ad libitum a commercial rodent diet (Harlan Teklad TRM Rat/Mouse Diet cat #: 2018SC), sterilized. Animals had free access to acidified autoclaved drinking water (pH 3.5) obtained from the municipality supply. |

Group and Experimental Design

Animals were divided into 4 groups as indicated in Table 3:

1—SD (Rotenone+SD); 2—SDA (Rotenone+SDA); 3—Control (Rotenone); 4—Naïve. The experimental groups were comprised of 6 animals for treated groups (1-3) and 2 animals in naïve group (4). Rotenone was administrated 3.0 mg/kg intraperitoneally (IP) once a day in the morning (days 1-9). SD 33 mg/kg and SDA 33 mg/kg were administrated intraperitoneally once a day in the afternoon (days 1-9).

Rearing behavior, rotarod and beam walk tests were performed before initiation of treatment (day 0) as well as on days 4, 8 and 10 of the experiment.

Animals weight was measured before initiation of treatment (day 0), on days 4, 7, 9 during the experiment and on termination day 11. On day 11, animals were sacrificed and brains were harvested for further histopathological analysis.

TABLE 3

Animal groups

| Group number | Number of animals | Material and | Route of administration |
|---|---|---|---|
| 1-SD | n = 6 (#13-18) | Rotenone (3 mg/kg) + SD (33 mg/kg) | IP |
| 2-SDA | n = 6 (#7-12) | Rotenone (3 mg/kg) + SDA (33 mg/kg) | IP |
| 3-Control | n = 6 (#1-6) | Rotenone (3 mg/kg) | IP |
| 4-Naive | n = 2 (#19-20) | None | None |

Experimental Procedures

Groups' Allocation:

On the last day of acclimation period, animals were allocated into treatment groups (3 rats in a cage) based on their body weight, while the average body weight was be similar in all treatment groups.

Figure 8:
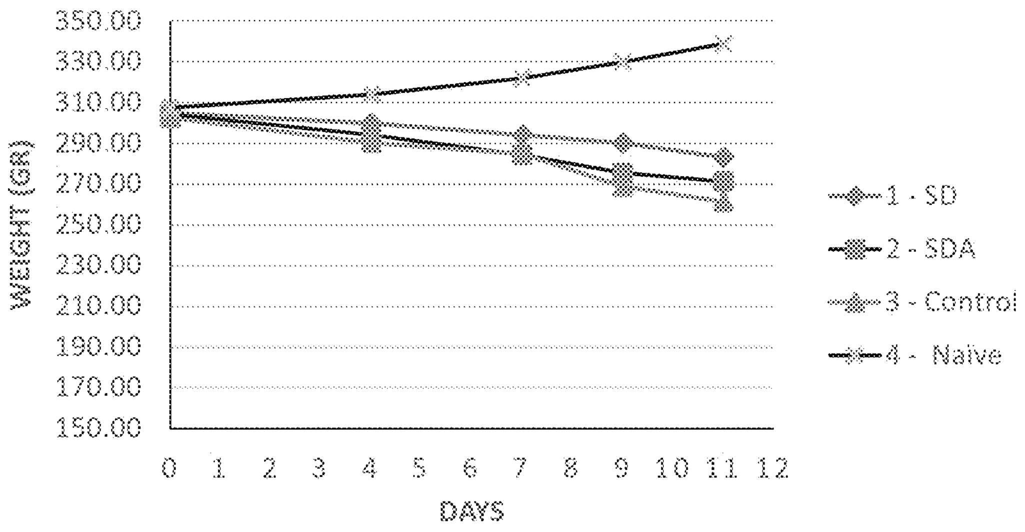
FIG. 8 summarizes animals body weights of rats treated with rotenone, a pesticide that by exerting mitochondrial stress mimics PD disease characteristics, and is widely used as a model of PD in rats and mice. Body weight of rats treated with rotenone with SD or SDA, and naïve rats.

Body Weight Monitoring:

All animals were weighed before dosing, weight measurements are presented in Table 4 and FIG. 8.

TABLE 4

Animals body weight

| Group | rat | Day 0<br>21 Aug. 2018<br>Weight (gr) | 4<br>25 Aug. 2018<br>Weight (gr) | 7<br>28 Aug. 2018<br>Weight (gr) | 9<br>30 Aug. 2018<br>Weight (gr) | 11<br>1 Sep. 2018<br>Weight (gr) |
|---|---|---|---|---|---|---|
| 1 - SD | 13 | 307 | 296 | 281 | 285 | 278 |
| | 14 | 294 | 290 | 286 | 280 | 284 |
| | 15 | 315 | 310 | 305 | 298 | 283 |
| | 16 | 300 | 299 | 294 | 286 | 274 |
| | 17 | 313 | 305 | 301 | 297 | 290 |
| | 18 | 300 | 299 | 298 | 295 | 290 |
| Average | | 304.83 | 299.83 | 294.17 | 290.17 | 283.17 |
| Std | | 7.51 | 6.36 | 8.35 | 6.82 | 5.84 |
| T-test 1-SD vs Control | | 0.068308 | 0.005668 | 0.003981 | 0.000042 | 0.001039 |
| 2 - SDA | 7 | 292 | 284 | 274 | 275 | 272 |
| | 8 | 307 | 293 | 283 | 272 | 261 |
| | 9 | 307 | 299 | 287 | 267 | 269 |
| | 10 | 305 | 294 | 283 | 274 | 266 |
| | 11 | 315 | 299 | 288 | 281 | 283 |
| | 12 | 300 | 296 | 291 | 284 | 277 |
| Average | | 304.33 | 294.17 | 284.33 | 275.50 | 271.33 |
| Std | | 7.06 | 5.08 | 5.41 | 5.62 | 7.18 |
| T-test 2-SDA vs Control | | 0.693888 | 0.166815 | 0.865534 | 0.176523 | 0.071247 |
| 3 - Control | 1 | 294 | 290 | 283 | 269 | 252 |
| | 2 | 306 | 286 | 279 | 263 | 250 |
| | 3 | 308 | 291 | 284 | 274 | 263 |
| | 4 | 295 | 290 | 286 | 255 | 261 |
| | 5 | 305 | 292 | 290 | 282 | 274 |
| | 6 | 308 | 293 | 287 | 270 | 268 |
| Average | | 302.67 | 290.33 | 284.83 | 268.83 | 261.33 |
| Std | | 5.88 | 2.21 | 3.44 | 8.43 | 8.40 |
| 4 - Näive | 19 | 305 | 313 | 325 | 334 | 346 |
| | 20 | 310 | 315 | 319 | 326 | 332 |
| Average | | 307.50 | 314.00 | 322.00 | 330.00 | 339.00 |
| Std | | 2.50 | 1.00 | 3.00 | 4.00 | 7.00 |

Drug Administration

IP administration: Rotenone was administrated to groups 1-3. Rotenone was injected intraperitoneally at a dose 3.0 mg/kg once a day in the morning (days 1-9). SD and SDA was administrated both at a dose of 33 mg/kg and were injected intraperitoneally once a day in the afternoon (days 1-9). Group number 4 was untreated, and remained as a naïve group.

Rat Rearing Behavior Test

Figure 9:
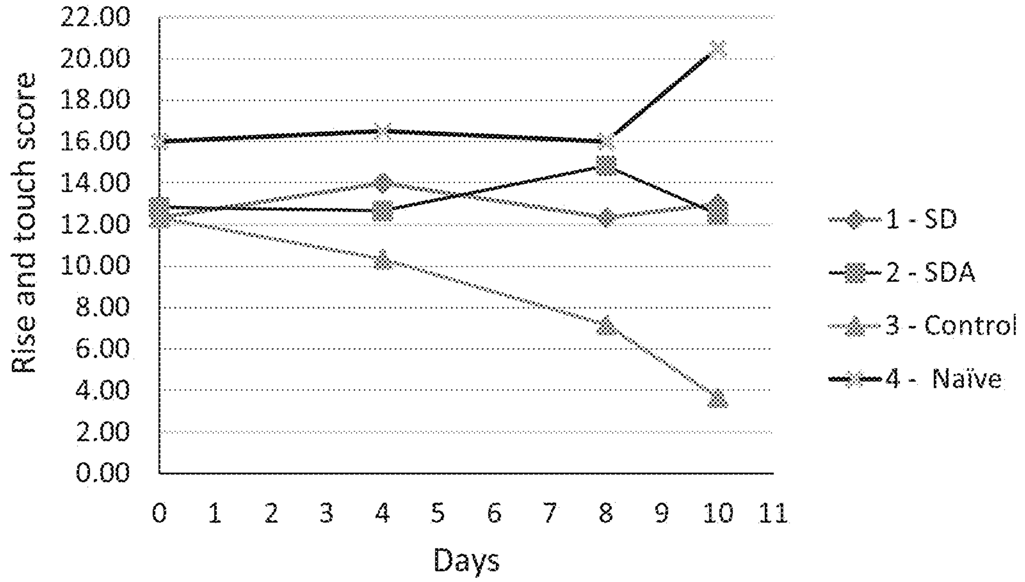
FIG. 9 provides rearing behavior test results in rats treated with rotenone alone, or in the presence of either SD or SDA and naïve rats. Rats treated with rotenone (3.0 mg/kg), with or without SD-444 (33 mg/kg) or SDA-341 (33 mg/kg). Rearing behavior in rats treated with rotenone alone, or in the presence of either SD or SDA and naïve rats treated with rotenone with SD or SDA, and naïve rats is shown at days 4, 8, and 10.

Animals were placed in a clear glass cylinder (40 cm high and 20 cm diameter) and number of rears in 2 min was observed. Rear was considered as animals raised their hands above the shoulder and made contact with the wall of cylinder with their forelimb. The results of rat rearing behavior test are presented in Table 5 and FIG. 9.

TABLE 5

Rearing behavior (cylinder) test results:

| Group | rat | Day 0<br>21 Aug. 2018<br>Cylinder rise and touch | 4<br>25 Aug. 2018<br>cylinder rise and touch | 8<br>29 Aug. 2018<br>cylinder rise and touch | 10<br>31 Aug. 2018<br>cylinder rise and touch |
|---|---|---|---|---|---|
| 1-SD | 13 | 8 | 9 | 10 | 13 |
| | 14 | 18 | 12 | 18 | 17 |
| | 15 | 9 | 13 | 15 | 9 |
| | 16 | 13 | 15 | 12 | 15 |
| | 17 | 13 | 13 | 10 | 8 |
| | 18 | 13 | 22 | 9 | 16 |
| Average | | 12.33 | 14.00 | 12.33 | 13.00 |
| Std | | 3.25 | 4.00 | 3.20 | 3.42 |
| T-test 1-SD VS Control | | 0.583 | 0.047 | 0.007 | 0.002 |
| 2-SDA | 7 | 18 | 14 | 15 | 11 |
| | 8 | 9 | 12 | 19 | 14 |
| | 9 | 12 | 14 | 8 | 9 |
| | 10 | 12 | 11 | 12 | 10 |

TABLE 5-continued

Rearing behavior (cylinder) test results:

| Group | rat | Day 0<br>21 Aug. 2018<br>Cylinder rise and touch | Day 4<br>25 Aug. 2018<br>cylinder rise and touch | Day 8<br>29 Aug. 2018<br>cylinder rise and touch | Day 10<br>31 Aug. 2018<br>cylinder rise and touch |
|---|---|---|---|---|---|
| | 11 | 18 | 15 | 16 | 14 |
| | 12 | 8 | 10 | 19 | 17 |
| Average | | 12.83 | 12.67 | 14.83 | 12.50 |
| Std | | 3.93 | 1.80 | 3.89 | 2.75 |
| T-test 2-SDA VS Control | | 0.838 | 0.136 | 0.054 | 0.002 |
| 3-Control | 1 | 8 | 9 | 6 | 0 |
| | 2 | 18 | 13 | 1 | 4 |
| | 3 | 13 | 14 | 8 | 1 |
| | 4 | 15 | 6 | 0 | 0 |
| | 5 | 8 | 10 | 8 | 8 |
| | 6 | 12 | 10 | 20 | 9 |
| average | | 12.33 | 10.33 | 7.17 | 3.67 |
| Std | | 3.59 | 2.62 | 6.54 | 3.68 |
| 4-Naïve | 19 | 14 | 15 | 18 | 25 |
| | 20 | 18 | 18 | 14 | 16 |
| average | | 16.00 | 16.50 | 16.00 | 20.50 |
| Std | | 2.00 | 1.50 | 2.00 | 4.50 |

Rotarod Behavior Assay

Figure 10:
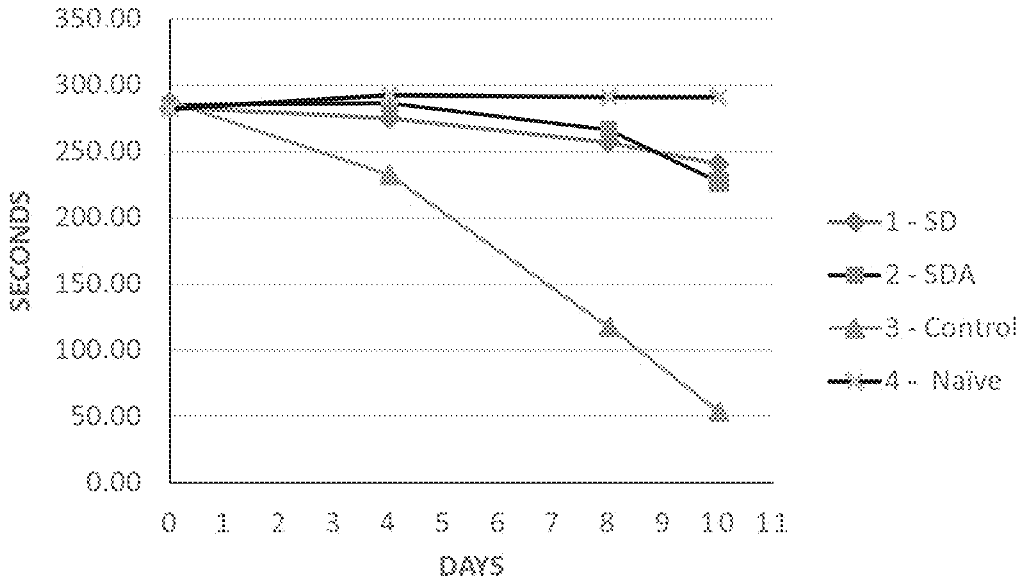
FIG. 10 provides rotarod results in rats treated with rotenone alone, or in the presence of either SD or SDA and naïve rats. Rats treated with rotenone (3.0 mg/kg), with or without SD-444 (33 mg/kg) or SDA-341 (33 mg/kg). Rotarod behavior was tested in rats treated with rotenone alone, or in the presence of either SD or SDA and naïve rats treated with rotenone with SD or SDA, and naïve rats is shown at days 4, 8, and 10.

The test was used to evaluate motor coordination and balance. Apparatus was set to accelerate from 4 to 40 rpm in 300 s, and animals from same cage are placed in separate lanes on rod initially rotating at 4 rpm. Rotarod test results are presented in Table 6 and FIG. 10.

TABLE 6

Rotarod results:

| group | rat | day 0<br>21 Aug. 2018<br>R.R (sec) | day 4<br>25 Aug. 2018<br>R.R (sec) | day 8<br>29 Aug. 2018<br>R.R (sec) | day 10<br>31 Aug. 2018<br>R.R (sec) |
|---|---|---|---|---|---|
| 1-SD | 13 | 280 | 268 | 251 | 255 |
| | 14 | 288 | 300 | 282 | 258 |
| | 15 | 300 | 300 | 267 | 266 |
| | 16 | 291 | 247 | 254 | 224 |
| | 17 | 267 | 255 | 237 | 192 |
| | 18 | 274 | 280 | 249 | 248 |
| average | | 283.33 | 275.00 | 256.67 | 240.50 |
| std | | 10.98 | 20.45 | 14.34 | 25.32 |
| T-test 1-SD VS Control | | 0.076115 | 0.000486 | 0.0000002 | 0.000116 |
| 2 - SDA | 7 | 278 | 298 | 281 | 270 |
| | 8 | 300 | 274 | 249 | 195 |
| | 9 | 269 | 263 | 234 | 123 |
| | 10 | 290 | 300 | 277 | 260 |
| | 11 | 300 | 300 | 268 | 243 |
| | 12 | 274 | 283 | 289 | 271 |
| average | | 285.17 | 286.33 | 266.33 | 227.00 |
| std | | 12.25 | 14.24 | 19.11 | 53.18 |
| T-test 2-SDA vs Control | | 0.708284 | 0.013093 | 0.000103 | 0.000357 |
| 3-Control | 1 | 282 | 250 | 78 | 0 |
| | 2 | 280 | 189 | 105 | 12 |
| | 3 | 300 | 230 | 132 | 108 |
| | 4 | 276 | 230 | 76 | 0 |
| | 5 | 289 | 292 | 192 | 88 |
| | 6 | 300 | 202 | 122 | 114 |
| average | | 287.83 | 232.17 | 117.50 | 53.67 |
| std | | 9.42 | 33.37 | 39.20 | 50.44 |
| 4- | 19 | 270 | 300 | 300 | 300 |

TABLE 6-continued

| Rotarod results: | | | | | |
|---|---|---|---|---|---|
| | | day | | | |
| group | rat | 0<br>21 Aug. 2018<br>R.R (sec) | 4<br>25 Aug. 2018<br>R.R (sec) | 8<br>29 Aug. 2018<br>R.R (sec) | 10<br>31 Aug. 2018<br>R.R (sec) |
| Naïve | 20 | 294 | 285 | 282 | 282 |
| average | | 282.00 | 292.50 | 291.00 | 291.00 |
| std | | 12.00 | 7.50 | 9.00 | 9.00 |

Rat Beam Walk Test

Figure 11:
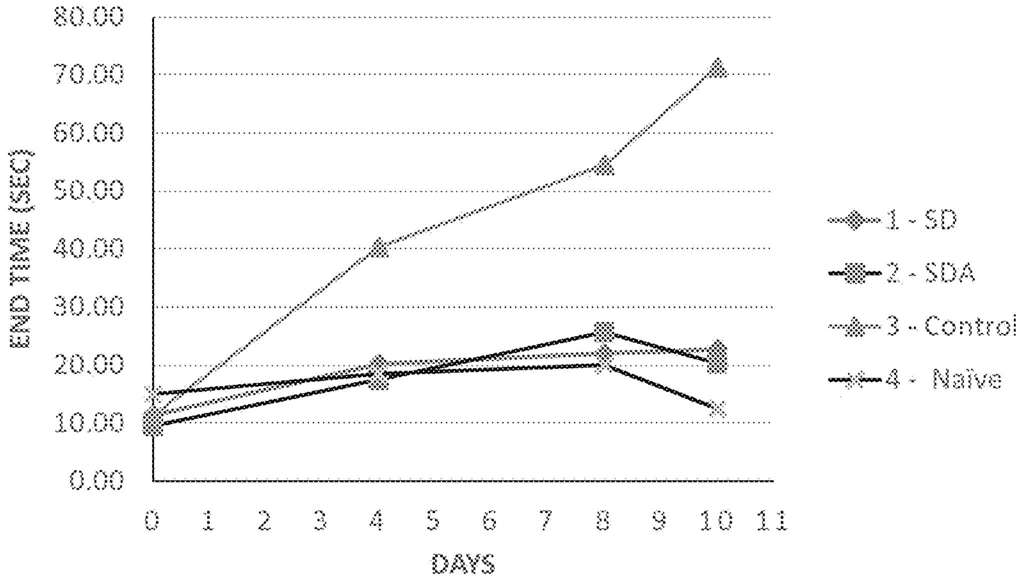
FIG. 11 provides rat beam walk test results in rats treated with rotenone alone, or in the presence of either SD or SDA and naïve rats. Rats treated with rotenone (3.0 mg/kg), with or without SD-444 (33 mg/kg) or SDA-341 (33 mg/kg). Walk beam behavior was tested in rats treated with rotenone alone, or in the presence of either SD or SDA and naïve rats treated with rotenone with SD or SDA, and naïve rats is shown at days 4, 8, and 10.

Animals were gently placed on 1 m long narrow aluminum beam facing one of the ends and allowed to walk to the end of the beam. The results of rat beam walk test are presented in Table 7 and FIG. 11.

TABLE 7

| Rat beam walk test results: | | | | | |
|---|---|---|---|---|---|
| | | Day | | | |
| Group | rat | 0<br>21 Aug. 2018<br>beam<br>end time(sec) | 4<br>25 Aug. 2018<br>beam<br>end time(sec) | 8<br>29 Aug. 2018<br>beam<br>end time(sec) | 10<br>31 Aug. 2018<br>beam<br>end time(sec) |
| 1-SD | 13 | 19 | 13 | 22 | 23 |
| | 14 | 5 | 15 | 18 | 17 |
| | 15 | 8 | 6 | 16 | 12 |
| | 16 | 10 | 38 | 21 | 27 |
| | 17 | 16 | 18 | 32 | 14 |
| | 18 | 10 | 31 | 23 | 43 |
| average | | 11.33 | 20.17 | 22.00 | 22.67 |
| Std | | 4.75 | 10.95 | 5.07 | 10.43 |
| T-test 1-SD VS Control | | 0.089 | 0.030 | 0.004 | 0.031 |
| 2-SDA | 7 | 7 | 12 | 16 | 22 |
| | 8 | 3 | 32 | 23 | 17 |
| | 9 | 10 | 14 | 52 | 34 |
| | 10 | 8 | 21 | 18 | 10 |
| | 11 | 12 | 10 | 19 | 21 |
| | 12 | 17 | 16 | 26 | 18 |
| average | | 9.50 | 17.50 | 25.67 | 20.33 |
| Std | | 4.35 | 7.34 | 12.23 | 7.23 |
| T-test 2-SDA vs Control | | 0.511 | 0.138 | 0.152 | 0.026 |
| 3-Control | 1 | 12 | 100 | 120 | 120 |
| | 2 | 8 | 25 | 33 | 52 |
| | 3 | 13 | 10 | 9 | 26 |
| | 4 | 19 | 44 | 86 | 120 |
| | 5 | 10 | 36 | 47 | 70 |
| | 6 | 6 | 27 | 32 | 40 |
| average | | 11.33 | 40.33 | 54.50 | 71.33 |
| Std | | 4.15 | 28.65 | 37.37 | 36.85 |
| 4-Naïve | 19 | 20 | 10 | 18 | 9 |
| | 20 | 10 | 27 | 22 | 16 |
| Average | | 15.00 | 18.50 | 20.00 | 12.50 |
| Std | | 5.00 | 8.50 | 2.00 | 3.50 |

Study Termination

Animals was euthanized by $CO_2$. Blood was collected and serum was separated. Organs (brains), 20 samples, from 20 rats, were harvested and fixed in 2.5% PFA. Brains were dissected to obtain sections from the Substantia Nigra Pars compacta (SNC) and the striatum (ST) using a rat brain matrix. After the dissection in a standard position per brain sections were put in an embedding cassette.

Study Results

In vitro-Studies in tissue culture showed that SD and SDA protect human neuroblastoma SH-SY5Y cells from oxidative stress induced by selectively inhibiting thioredoxin reductase by auranofin (AuF). AuF triggers activation of MAPKs pathway through the phosphorylation JNK and p38. The two compounds SD-444 and SDA-341 inhibit JNK and p38 phosphorylation and thereby inhibitg the apoptotic pathway. Preventing apoptosis was accompanied by increasing cell-viability shown in phase microscopy.

In vivo—Parkinsonian features, such as loss of dopaminergic neurons in the substantia nigra and motor impairment are demonstrated by exposure of rats to rotenone. Rotenone exerts mitochondrial stress and is widely used as a model for PD.

Using the rotenone rat model, both SD-444 and SDA-341 when administered intraperitoneally, appeared to rescue motor activity in the three motor tests the rotarod, the cylinder, and the walk-beam tests.

The goal of Walk-beam test is to evaluate motor balance and to show the ability of the rat to stay upright and walk across an elevated narrow beam to a safe platform. This task is particularly useful for detecting subtle deficits in motor skills and balance that may not be detected by other motor tests, such as the Rotarod. As shown both SD and SDA were very effective in this test, reversing the rotenone induced imbalance.

The Cylinder test is designed to evaluate locomotor asymmetry in rodent models of CNS disorders like the rotenone. It can be used to evaluate novel chemical entities for their effect on motor performance. Here we have shown that SD and SDA were very effective in maintaining locomotactivity in Rotenone-treated rats.

The rotarod test motor coordination has been assessed also by the rotarod-test that is based on a rotating rod with forced motor activity. The assay that evaluates balance, grip strength, and motor coordination, showed that SD and SDA significantly reversed motor dysregulation mediated by rotenone. Both compounds significantly improved balance, grip strength, and motor coordination.

In summary, our studies showed that SD and SDA increase viability of neuronal cells in vitro and inhibit the MAPK apoptotic pathway. Both SD and SDA appeared to be effective anti-apoptotic reagents, manifested by inhibiting the AuF-induced MAPKs phosphorylation reversing the AuF oxidative stress effects.

In vivo, they effectively improved motor performance, reversing the rotenone impaired motor performance, which is induced by mitochondrial stress. Rescue activity was shown in three motor tests. Hence, SD and SDA could potentially become effective in treating neurodegenerative diseases and neurodegenerative related-disorders.

The invention claimed is:

1. A method of ameliorating one or more motor symptoms of Parkinson's disease in a subject in need thereof, the method comprising administering to the subject a therapeutically effective amount of the compound of formula I:

(I)

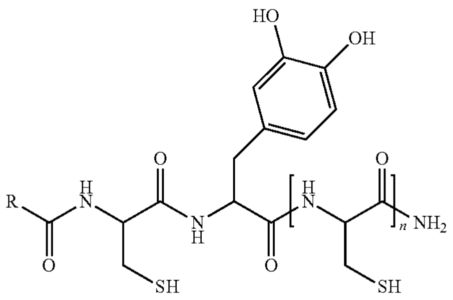

wherein R is a methyl; and n is 1.

* * * * *